United States Patent
Fukuzawa (10) Patent No.: US 7,203,266 B2
(45) Date of Patent: Apr. 10, 2007

(54) IMAGE DISPLAY METHOD AND METHOD FOR PERFORMING RADIOGRAPHY OF IMAGE

(75) Inventor: Kaori Fukuzawa, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 100 days.

(21) Appl. No.: 10/508,652

(22) PCT Filed: Mar. 14, 2003

(86) PCT No.: PCT/JP03/03062

§ 371 (c)(1),
(2), (4) Date: Jul. 11, 2005

(65) Prior Publication Data

US 2006/0013461 A1    Jan. 19, 2006

(30) Foreign Application Priority Data

Mar. 26, 2002    (JP)    ............................ 2002-085093

(51) Int. Cl.
*H05G 1/00*    (2006.01)
(52) U.S. Cl. .......................................... 378/4; 382/132
(58) Field of Classification Search .................... 378/4, 378/62, 98, 210, 901; 382/128, 131, 132
See application file for complete search history.

(56) References Cited

U.S. PATENT DOCUMENTS 5,218,623 A    6/1993    Toki et al. ...................... 378/4

FOREIGN PATENT DOCUMENTS

| EP | 0485999 A1 | 5/1992 |
|---|---|---|
| EP | 0884697 A2 | 12/1998 |
| JP | 4-180739 | 6/1992 |
| JP | 8-166995 | 6/1996 |
| JP | 9-35043 | 2/1997 |
| JP | 10-52423 | 2/1998 |
| JP | 11-409 | 1/1999 |

*Primary Examiner*—Courtney Thomas
(74) *Attorney, Agent, or Firm*—Cooper & Dunham LLP (57) ABSTRACT

CT images are interpreted while being displayed in order (STEP S16), and when a CT image is observed in which the presence of a lesion is suspected, an "Add Marker" button is clicked to add a marker to that CT image (STEPS S18, S20). By means of the click operation, a marker is automatically added at a slice position on a scanogram that corresponds to the CT image (CT image requiring precise examination) in which the presence of a lesion is suspected. By automatically adding a marker at a desired slice position on a scanogram in this manner, it is possible to set scanning conditions for the purpose of a precise examination while viewing the marker on the scanogram (STEP S24). It is thus possible to accurately set a range for precise examination by a simple operation in a short time.

12 Claims, 11 Drawing Sheets

(1) Observation of screening images

Scanogram

CT image

(2) Operator presses "Add Marker" button when lesion is suspected

(3) Marking of slice position

Marker and slice position information are added

Marker is added

FIG. 4

(1) Operator sets slice positions of precision examination while viewing markers

(1) Observation of images

Scanogram    CT image (2) Operator presses "Add Marker" button when rescan is required (3) Marking of slice position Marker and slice position information are added    Marker is added Scanogram    CT image Rescanning is enabled (4) Presses "Rescan Marked Position" button

(1) Click marker

IMAGE DISPLAY METHOD AND METHOD FOR PERFORMING RADIOGRAPHY OF IMAGE

TECHNICAL FIELD

The present invention relates to a method for displaying images and a method for performing radiography of image, and more particularly to a method for displaying images and a method for performing radiography of image that can simply carry out instructions concerning a tomogram of a subject in doing a precise examination or rescan.

BACKGROUND ART (1) Method of Setting a Range for Precise Examination in CT (Computed Tomography) Examination In a CT examination, a scanogram is taken first, and slice positions and a range are subsequently determined based on the scanogram before taking CT images. Next, screening (assessment of the presence or absence of a lesion) is performed using the CT images to perform a precise examination. Hereinbelow, the term "precise examination" refers to an examination that is performed in a CT examination with the purpose of observing a lesion when the presence of a lesion is suspected based on the results of screening.

When performing a precise examination, imaging conditions are set to obtain more detailed and clearer CT images than images obtained by screening, and then CT images are taken again. In an example of examining lung, images are taken for screening by employing a slice thickness of 10 mm and a table speed of 10 mm, while in a precise examination images of only a region where existence of lesion is suspected in the screening are produced again by employing a slice thickness of 2 mm and a table speed of 2 mm.

Although in screening an imaging range is generally set to cover all the organs, in a precise examination only a region where existence of a lesion is suspected is usually set as an object of imaging. This is because taking an image again in a precise examination of a region where a lesion is not observed in screening would constitute unnecessary radiation exposure. Accordingly, the range of imaging in a precise examination is determined on the basis of the slice position of the CT images obtained by screening.

Figure 11:
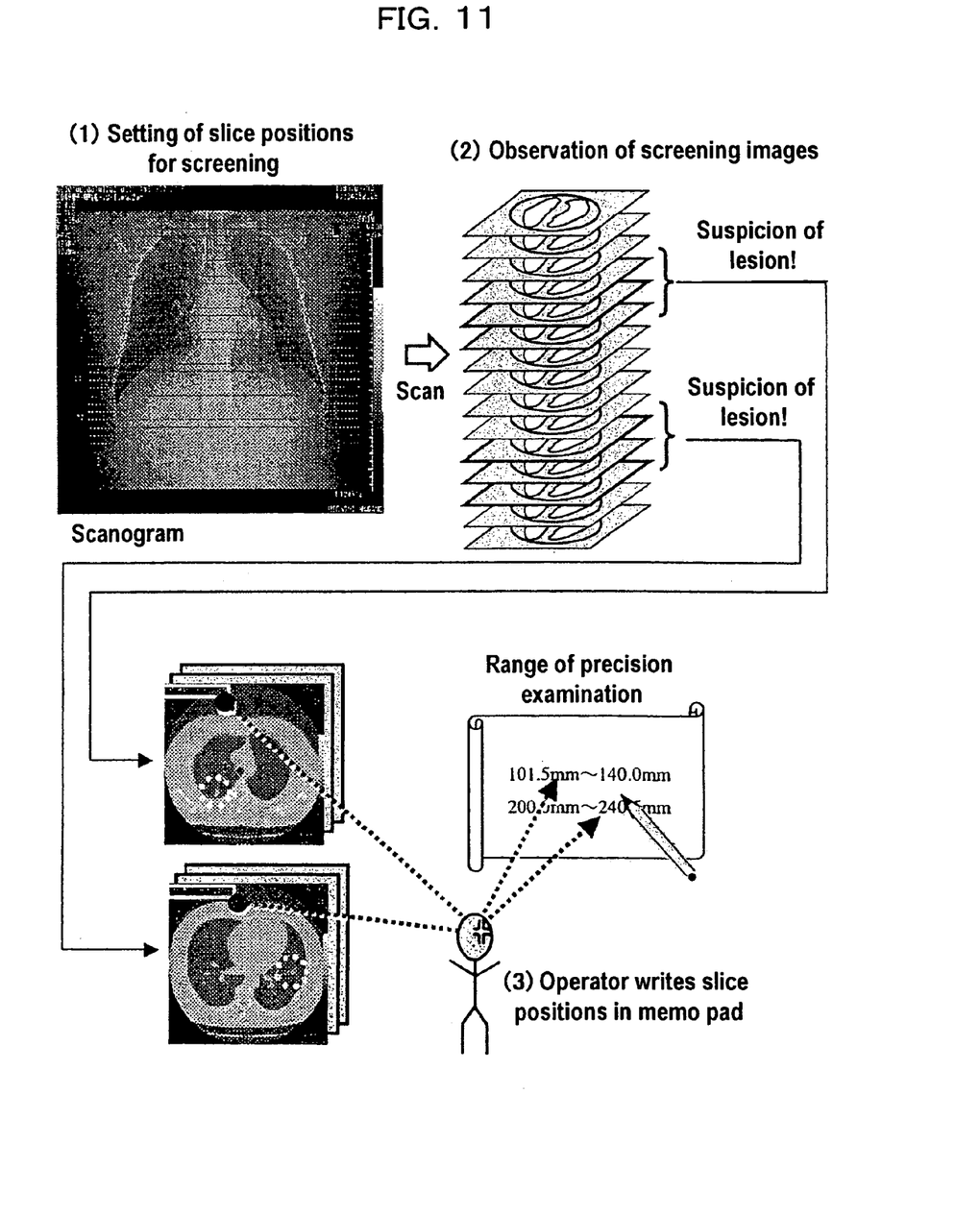
FIG. 11 is a view used to describe a conventional method of observing CT images obtained in screening and transcribing a range for precise examination into a memo pad.
Figure 12:
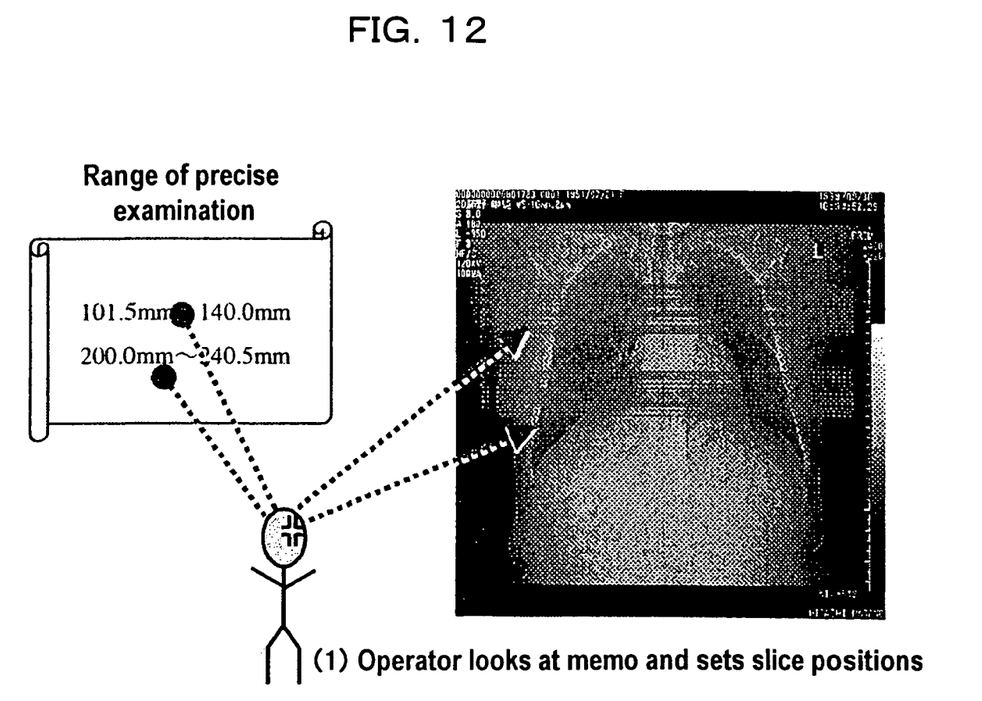
FIG. 12 is a view used to describe a conventional method of setting a range for precise examination from numbers written into a memo pad.

When setting the scanning conditions for a conventional precise examination, based on the results of observation of CT images obtained in screening (FIGS. 11(1) and 11(2)), the operator transcribes the slice positions of the CT images where existence of a lesion is suspected into a memo pad (FIG. 11(3)) (depending on the sizes or number of lesions, a plurality of slice positions may be transcribed). Then, as shown in FIG. 12, the operator sets the slice positions while looking at the slice positions written in the memo pad. Since the slice positions are written with 5 digits or more, such as 1234.5 mm, it is difficult to remember the slice position mentally, and therefore many operators transcribe the positions into a memo pad.

Most current X-ray CT apparatuses employ a GUI (Graphical User Interface). Therefore, when observing images many operators hold a "mouse" in their dominant hand (the right hand in many cases). However, in order to transcribe a slice position into a memo pad, the operator must release the mouse from their dominant hand to hold a pen and write down the slice position in the memo pad. Then, when observing the screening images again, the operator must put down the pen and hold the mouse again. Thus, there is a problem that in order to record a range for a precise examination in a memo pad, an operator must switch holding a mouse over to holding a pen several times.

Further, in screening, a mistake may occur when a operator transcribes a slice position of CT image where existence of a lesion is suspected into a memo pad. There is also a possibility of a mistake occurring when setting slice positions for a precise examination based on the figures written into the memo pad.

Furthermore, in the conventional method using a memo pad, due to the complexity of the operations, a substantial time is required to set the scan conditions for changing from screening to precise examination. During the time period taken to change from screening to precise examination, the subject to be examined is not allowed to move from the table to avoid inconformity of slice positions between screening and precise examination, whereby the time for setting the scan conditions of the precise examination is weariness for the subject.

(2) Method of Setting a Slice Position for Rescanning in CT Examination

When an artifact appears in a specific CT image owing to a certain cause, such as movement of the subject, in a conventional technique, the operator first records the slice position of the CT image in which the artifact appears in a memo pad. Thereafter, the operator sets the slice position to be re-scanned while looking at the slice position written in the memo pad. In a similar manner to the above method (1), the operator must switch holding a mouse over to holding a pen several times in order to record the slice position to be re-scanned in the memo pad. There is a problem that recording these slice positions in a memo pad during the examination that requires speed is troublesome and complicated.

There also is a possibility that a mistake will be made when transcribing the positions of re-scanning in a memo pad or when setting the positions for rescanning based on the transcribed positions. Furthermore, for the same reasons as in the above (1), the operations involved in setting the slice positions of re-scanning require a lengthy time period and make the subject wearied.

(3) Method for Marking an Image to be an Important Factor in Diagnosis and a Method for Displaying the Image with the Marker in CRT Diagnosis The term "CRT diagnosis" refers to displaying an image on a CRT (Cathode Ray Tube) to perform diagnosis without developing the image on film. In CRT diagnosis, an observer adds remarks to several CT images having clincher for diagnosis among a series of images, and stores the images and remarks as electronic data. When adding the remarks, text data are used as a means of adding character information, and ROI (Region of Interest), distance measurement, angle measurement, straight lines, curved lines, arrows and the like are used as a means for adding graphical information.

When the stored electronic data of the stored series of images and remarks are read out again, CT images to which no remark is attached are displayed as they are, and CT images to which the remark is attached are displayed together with the character information and/or graphical information.

Attaching the text data, ROI, distance measurement, angle measurement, straight line, curved line, arrow or the like to the CT image, suffice it to say that play the role of "adding a marker (remark) to a CT image". However, while the function that adds these kinds of character information and graphical information is to indicate and measure a lesion visualized in a CT image, it is not a function of indicating the CT image of diagnostic importance itself.

In CRT diagnosis, there are cases where it is more appropriate that an observer adds neither character information nor graphical information to a lesion visualized on several CT images having diagnostic clincher among a series of CT images. For example, when observing a state that a tumor is stained by a contrast medium according; to a lapse of time, or when observing a state where a tumor is gradually becoming small as a result of periodic observation or the like, observation is facilitated when superfluous characters or graphics are not displayed on the CT image.

In this case, rather than adding a marker to the lesion on the CT image, it is more appropriate to add a marker to the CT images of diagnostic importance. However, that type of method has not existed up to now. Therefore, when observing a state that a tumor is stained by a contrast medium according to a lapse of time in the conventional method, the observer observes CT images that are seemingly considered to be of the same slice position, whereby there is a problem that the method lacks certitude. Furthermore, when stored electronic data for a series of images and remarks are read out again, CT images to which the remark is not attached are displayed as they are, and CT images to which the remark is attached are displayed together with the character information and/or graphical information.

When adding a marker to a CT image in the conventional method, text data, ROI, distance measurement, angle measurement, straight line, curved line, arrow or the like is used as the marker. Because keyboard operation or mouse operation involving several steps is respectively required to add the marker, these are not suitable for the purpose of adding the marker to the CT image itself.

Furthermore, when a series of image data is readout that includes a CT image to which a remark was added, in order to display the CT image having the remark out of the plurality of images, it is necessary for an operator to check images one by one starting from the first image to locate the image with the remark in it. It has thus been necessary to carry out image update operations several times until the CT image with the remark in it is displayed. Furthermore, when there is a plurality of CT images of diagnostic importance, there has been a drawback that a position where the images with the remark in it (images of diagnostic importance) is unknown until all the images are displayed at once.

(4) Method of Adding Markers to Images of Diagnostic Importance and Filming the Images (Printing the Images on Photographic Film) in CT Examination In a similar manner to CRT diagnosis, in diagnosis using film an observer adds remarks to several CT images having clincher in diagnosis out of a series of film. When viewing the film to diagnose, particular attention is paid to CT images to which the observer has added remarks among the series of CT images.

In a conventional technique, in the same manner as in the CRT diagnosis of the above (3), text data, ROI, distance measurement, angle measurement, straight line, curved line, arrow or the like is also added to the CT images for filming.

In a conventional technique, no method of adding a marker to the CT image having diagnostic clincher exists other than adding a remark to a CT image on film.

Further, in the conventional technique, when explaining a treatment area or an examination area to a subject, because the difference between abnormality and normality is not known by the average subject, it has been necessary for a physician to write directly on a frame of film or to attach a piece of paper or the like. However, it is not preferable from the viewpoint of maintaining the medical information to afterward process the film.

With respect to filming, as in the above (3), when adding a marker to a CT image, text data, ROI, distance measurement, angle measurement, straight line, curved line, arrow or the like is used as the marker as in the above (3) since keyboard operations or mouse operations involving several steps are respectively required for each type of the marker, these types are not suitable for the purpose of adding a marker to a CT image itself.

The present invention is provided in view of the foregoing, and it is an object of the invention to provide a method for displaying images and a method for performing radiography of image that make it possible to accurately set of a range for precise examination and slice positions for rescanning in a short time by a simple operation.

Another object of the present invention is to provide a method for displaying images that easily displays a tomogram of an important factor for diagnosis certainly at the same tomographic position, or for filming as such.

DISCLOSURE OF THE INVENTION

In order to achieve the above objects, the present invention provides a method for displaying images that displays a scanogram used for determining a scanning range of a subject to perform radiography to obtain tomograms and also displays tomograms of a plurality of slice positions within a scanning range determined using the scanogram, comprising steps of: sequentially displaying the plurality of tomograms to interpret the tomograms, designating tomograms for precise examination or rescanning while interpreting the displayed tomograms, and adding a marker at slice positions on the scanogram corresponding to the designated tomograms.

According to the present invention, a scanogram and tomograms are displayed for screening. The scanogram and tomograms may be displayed on a screen at the same time, or may be displayed separately by switching screens. The tomograms are then interpreted while being sequentially displayed, and when a tomogram having a susupect lesion on it or a tomogram having an artifact on it is observed, an instruction is given to add a marker to the tomogram in question. For example, the observer may click an "Add Marker" button. By this input of an instruction, a marker is automatically added to the slice position on the scanogram corresponding to the designated tomogram. A marker may also be added to the designated tomogram itself. By automatically adding a marker at a predetermined slice position on a scanogram in this manner, a range for a precise examination or slice positions for rescanning can be set while viewing the marker on the scanogram.

Preferably, positional information indicating the slice position is added together with the marker for the slice position added to the scanogram. Therefore, it is no longer necessary to write positional information indicating the slice position into a memo pad.

Preferably, positional information indicating the slice position of the designated tomogram is stored in a storage device.

To achieve the aforementioned objects, the present invention comprises steps of performing radiography at a first slice thickness to obtain a plurality of tomograms from a predetermined scanning range of a subject, displaying in order the imaged plurality of tomograms to interpret the tomograms, designating tomograms for precise examination while interpreting the displayed tomograms, automatically setting a range for precise examination within the predetermined slice range based on slice positions of the designated tomograms, and performing imaging of the automatically set range for precise examination at a second slice thickness that thinner than the first slice thickness.

Although an operator may set the range for precise examination manually on the basis of markers added to a scanogram, according to the present invention a range for precise examination is automatically set on the basis of instructions input of a tomogram subject to precise examination, and imaging is automatically carried out using that range as the scanning conditions for the precise examination.

Preferably, the method further comprises a step of taking a scanogram of the subject in order to determine the predetermined scanning range.

Preferably, the step of designating tomograms to be subject to precise examination designates two tomograms as the first and last tomogram of precise examination, and the step of automatically setting the range for precise examination sets the region between the slice positions of the two tomograms as the precise examination range. Alternatively, the step of designating tomograms to be subject to precise examination designates one tomogram to be subject to precise examination, and the step of automatically setting the range for precise examination sets a predetermined range that includes the one tomogram and tomograms prior to and after the one tomogram as the precise examination range. As another alternative, the step of designating tomograms to be subject to precise examination designates a plurality of tomograms to be subject to precise examination, and the step of automatically setting the range for precise examination sets a range that covers the plurality of tomograms as the precise examination range.

To achieve the aforementioned objects, the present invention further provides a method for displaying images that displays a scanogram used for determining a slice range or slice positions of a subject to perform radiography to obtain tomograms, and also displays tomograms of a plurality of slice positions taken within a slice range that is determined using the scanogram, comprising steps of: sequentially displaying the plurality of tomograms to interpret the tomograms, designating tomograms as important factors in diagnosis while interpreting the displayed tomograms, and adding a first marker at slice positions on the scanogram that correspond to the designated tomograms.

According to the present invention, when a tomogram is designated as an important factor for diagnosis while interpreting tomograms sequentially displayed, a first marker is added at the slice position on the scanogram corresponding to the designated tomogram.

Preferably, the method further comprises a step of displaying the tomogram at a slice position of one of the first markers when the one is arbitrarily designated out of the first markers on the scanogram. More specifically, when an arbitrarily designated first marker is on the scanogram at the time of another interpretation, the tomogram (tomogram of diagnostic importance) for the slice position indicated by the designated first marker is displayed. This step is advantageous when diagnosis is performed by a plurality of interpreters.

Preferably, a second marker is added to the designated tomogram to indicate including an important factor for diagnosis.

Preferably, the method has a step of printing a scanogram on which the first marker is added and a view of tomograms to which the second marker is added on film. Accordingly, tomograms of diagnostic importance and the slice positions for those tomograms on a scanogram can be apparently seen in images printed on the film.

BEST MODE FOR CARRYING OUT THE INVENTION

Hereinbelow, preferred embodiments of a method for displaying images and a method for performing radiography of image according to the present invention are described in reference of the attached drawings.

Figure 1:
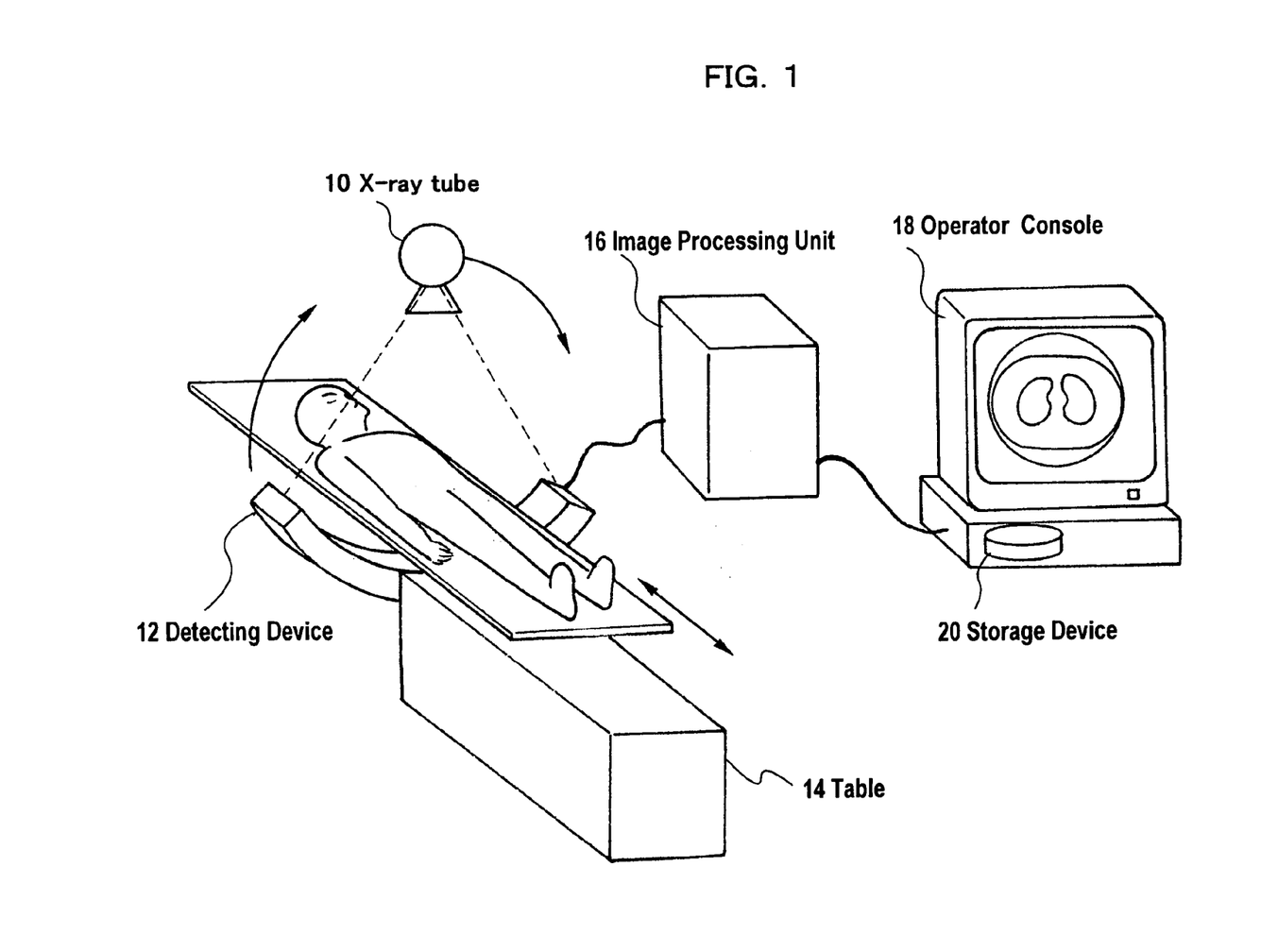
FIG. 1 is a schematic diagram showing a hardware configuration of an X-ray CT apparatus to which a method for displaying images and a method for imaging of the present invention are applied.

FIG. 1 is a schematic diagram showing a hardware configuration of an X-ray CT apparatus to which the method for displaying images and method for performing radiography of image according to the present invention are applied.

As shown in FIG. 1, the X-ray CT apparatus includes an X-ray tube 10, a detecting device 12, a table 14, an image processing unit 16 and an operator console 18.

The X-ray tube 10 and the detecting device 12 are disposed so as to face each other, and when taking a tomogram (CT image) they revolve around the circumference of the table 14 on which a subject is positioned. X-rays radiated from the X-ray tube 10 penetrate through the subject and the table, and are detected by the detecting device 12. Signals detected by the detecting device 12 is subject to pre-processing and image configuration processing in the image processing unit 16 to create a CT image.

CT images created in this manner are displayed on a CRT monitor in the operator console 18 and are also stored as image data in a storage device 20 in the operator console 18.

The method for displaying images of the present invention is not limited to an X-ray CT apparatus that performs CT imaging and displays the obtained CT images or scanogram, and the method can also be applied to an image display apparatus that has a function for displaying CT images.

More specifically, an image display apparatus is an apparatus including only the operator console 18 part of the X-ray CT apparatus. While an X-ray CT apparatus stores image data created by the image processing unit 16 in the storage device 20 of the operator console 18, an image display apparatus stores image data in the storage device 20 of the operator console 18 via a network or storage medium. The display of images, distance measurement of lesions displayed on an image, input of comments and the like can be performed using the operator console 18, and these types of added data can be stored together with the image data.

In recent years, there has been an increase in the number of hospitals that carry out so-called CRT diagnosis, in which images are not printed onto film but are stored as electronic data to observe the images on an image display apparatus. An image display apparatus is used in various situations in such hospitals, for example, when a physician interpreting the images adds a comment thereto, when a physician is delivering diagnosis, when a physician is explaining the condition of a disease to a subject, or when past images are compared with current images.

Next, embodiments of the method for displaying images and method for performing radiography of image of the present invention will be described.

(1) Method for Setting Range of Precise Examination in CT Examination

Figure 2:
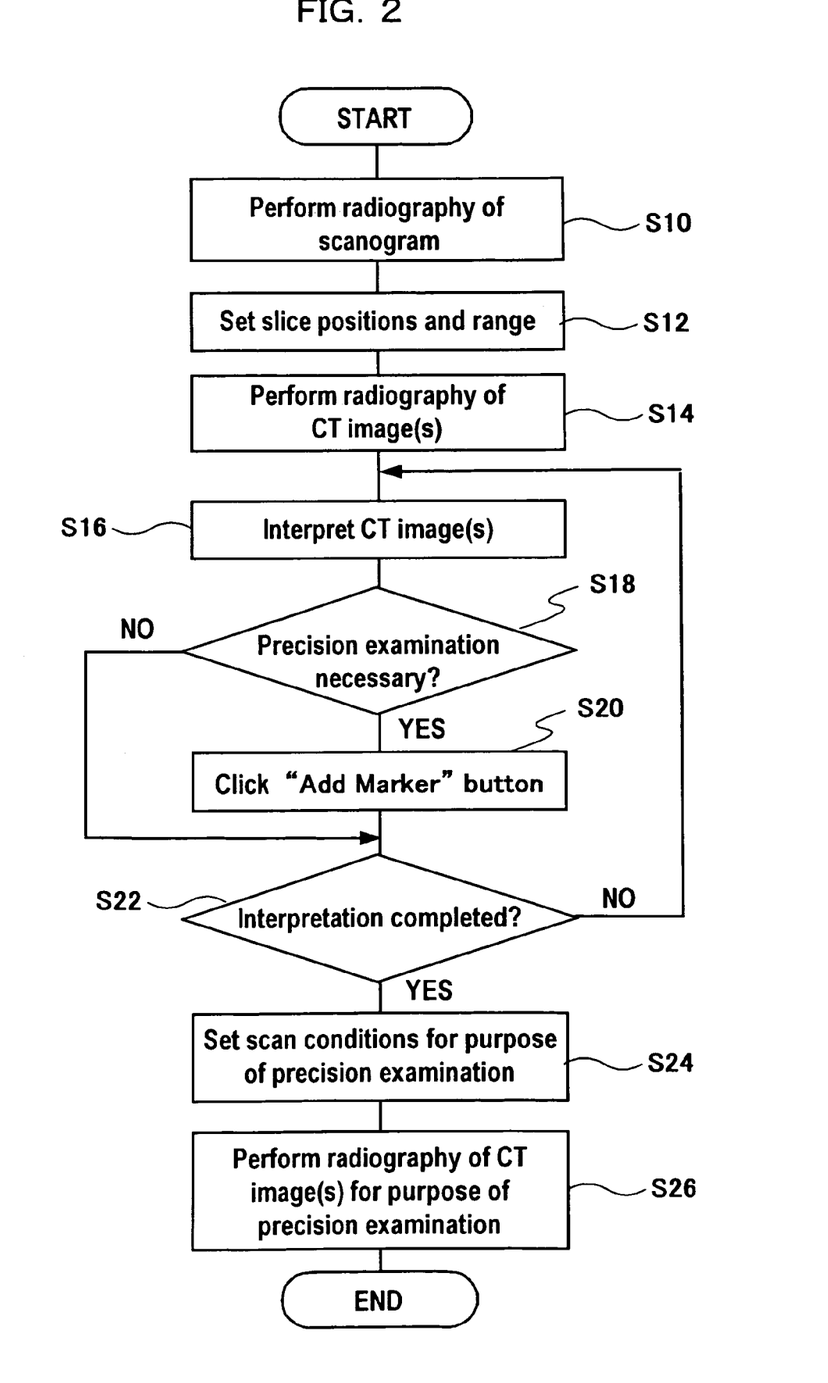
FIG. 2 is a flowchart illustrating an embodiment of procedures for setting a range for precise examination according to the present invention.

FIG. 2 is a flowchart showing an embodiment of the procedures for setting the range of a precise examination according to the present invention.

<STEP S10>

A screening image is taken for positioning use for the purpose of performing screening.

Figure 3:
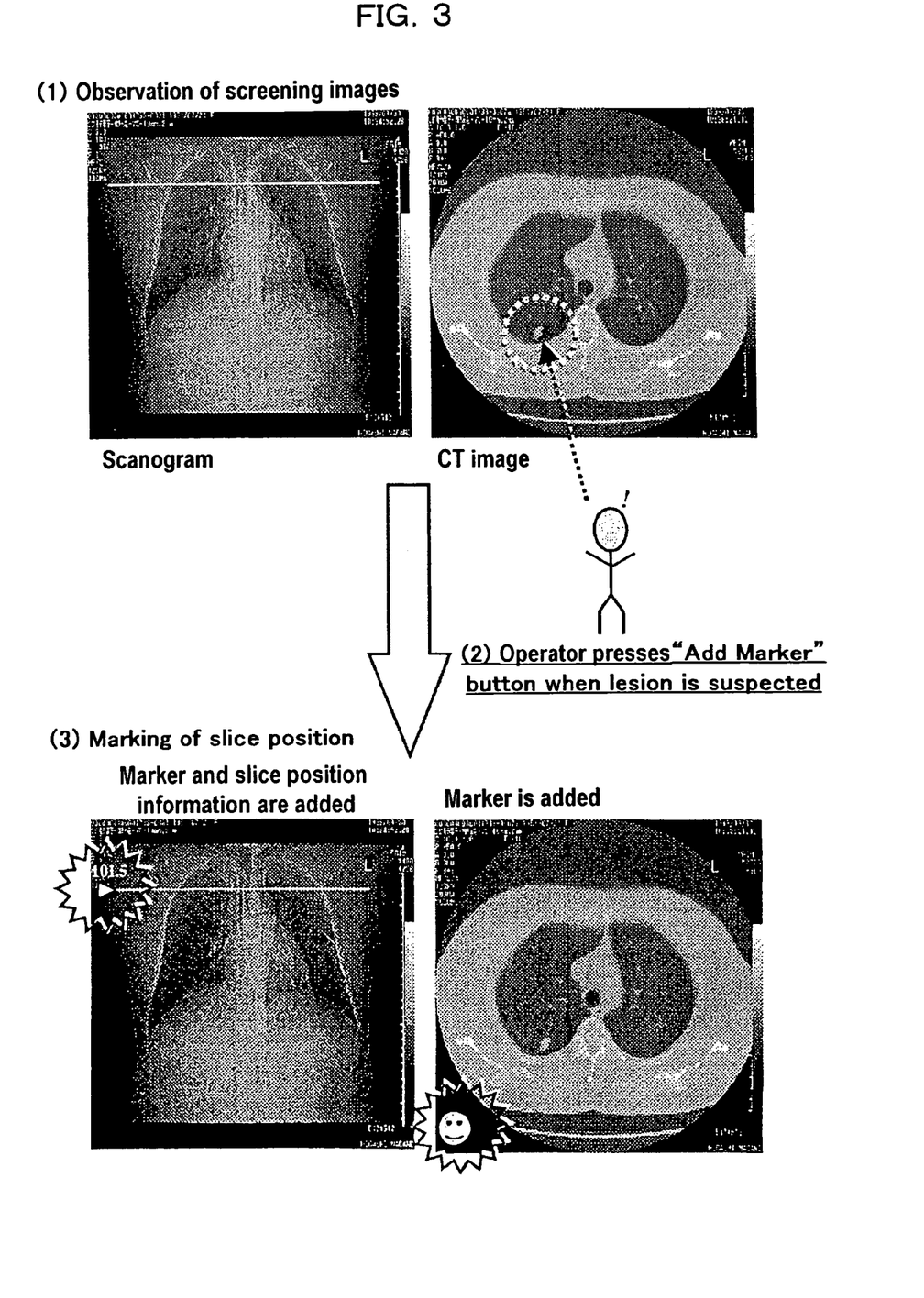
FIG. 3 is a view used to describe operations performed to add a marker to a CT image having a suspect lesion.

As shown in FIG. 3(1), a scanogram is an X-ray image that is sequentially taken first to accurately perform radiography for the range of an organ of interest. A scanogram is created by radiating X-rays while moving only the table 14 on which the subject is positioned, without rotating the X-ray tube 10 and the detecting device 12.

<STEP S12>

On the scanogram obtained in the preceding step, the slice positions and range of images for screening are set. This setting can be performed by inputting figures that indicate the slice positions or range using a keyboard or by designating slice positions using a mouse.

<STEP S14>

CT imaging is performed for the slice positions and range set in the preceding step. CT imaging is performed by rotating the X-ray tube 10 and detecting device 12 and radiating X-rays. Two patterns may be employed for the CT imaging: one is an imaging pattern in which X-ray radiation and table movement are repeated alternatively, and the second is an imaging pattern in which the table 14 is moved continuously while X-rays are continuously radiated thereto.

<STEP S16>

The thus-obtained CT images and scanogram are observed (interpreted) (FIG. 3(1)).

<STEP S18>.

After interpreting the CT images, judgment is made as to whether there is the suspicion of a lesion (i.e., whether or not a precise examination is necessary).

<STEP S20>

When a precise examination is necessary, the operator clicks on an "Add Marker" button (for example, a software button displayed on the monitor) using the mouse (FIG. 3(2)). If a precise examination is not required, the operation jumps to STEP S22.

When the "Add Marker" button is clicked, a marker is added to the CT image and a marker and slice position information are added to the scanogram (FIG. 3(3)). Further, the slice position of the CT image that was clicked is stored in the storage device 20 or the like.

<STEP S22>

Judgment is made as to whether all the CT images have been interpreted or not. If all the images have not been interpreted, the CT images are advanced by one frame and the process from STEP S16 to STEP S20 is repeated.

<STEP S24>

Figure 4:
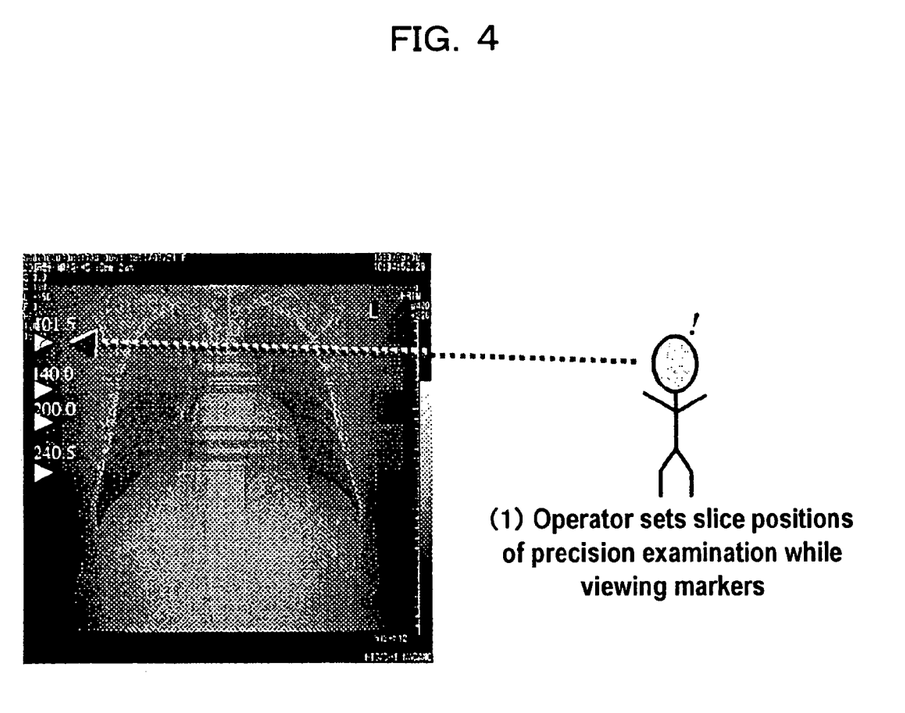
FIG. 4 is a view illustrating a method of setting a range for precise examination while viewing positional information and markers on a scanogram.

The setting of scan conditions for the purpose of precise examination is performed. As shown in FIG. 4, the slice positions are set while viewing the markers and positional information on the scanogram. More specifically, since slice positions and numerical values for CT images in which a lesion is suspected to be present are displayed on the scanogram, the range for the precise examination is set manually based on the scanogram.

<STEP S26>

CT imaging is performed for the purpose of precise examination with respect to the set range for precise examination. CT imaging for the purpose of precise examination is performed after setting the imaging conditions (slice thickness and table speed) so as to obtain CT images that are more detailed and clearer in comparison to images obtained in CT imaging for the purpose of screening.

Although in the present embodiment a case has been described in which a range for precise examination is set manually on the basis of markers and slice position information displayed on a scanogram, the present invention is not limited thereto, and imaging may be carried out automatically by checking off CT images where a lesion is suspected to be present to automatically set a range for precise examination and perform radiography employing that range as the scan conditions for the precise examination.

Automatic setting of the precise examination range may be performed by a method in which two CT images that correspond to the first and last slice positions of the precise examination are checked off, a method in which one CT image is checked off and a predetermined range including that CT image and CT images prior to and after that CT image is set as the precise examination range, or a method in which, when a plurality of CT images have been checked off, a range that covers all of the checked off CT images is set as the range for precise examination. Further, when automatically setting a precise examination range, the display of markers or slice positions on the scanogram can be omitted.

(2) Method of Setting Slice Positions for Rescanning in CT Examination

When performing a CT examination, sometimes an artifact appears in only the CT image for a specific slice position due to some cause, such as movement by the subject during imaging. When this happens, imaging is performed again for only the same position as that of the CT image in which the artifact appeared. This type of imaging is referred to as "rescanning".

Figure 5:
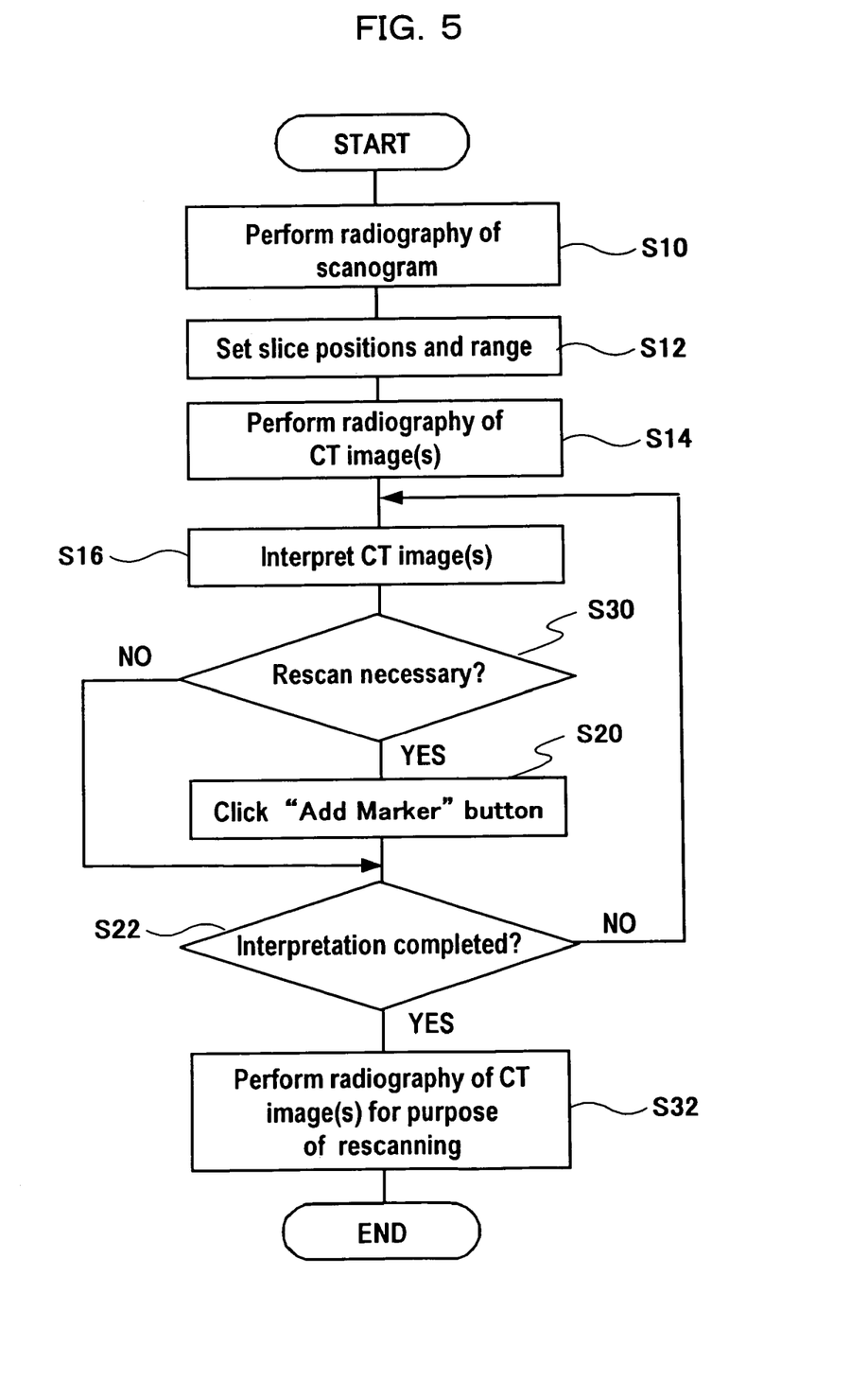
FIG. 5 is a flowchart illustrating an embodiment of procedures for setting re-scanning slice positions according to the present invention.

FIG. 5 is a flowchart showing an embodiment of the procedures for setting slice positions for rescanning according to the present invention. The steps therein that are common with the flowchart shown in FIG. 2 have been given the same step number, and a detailed description of these steps is omitted.

The flowchart shown in FIG. 5 differs from the flowchart shown in FIG. 2 in that in place of STEP S18, STEP S24 and STEP S26 in FIG. 2, the processes of STEP S30 and STEP S32 are carried out.

<STEP S30>

Figure 6:
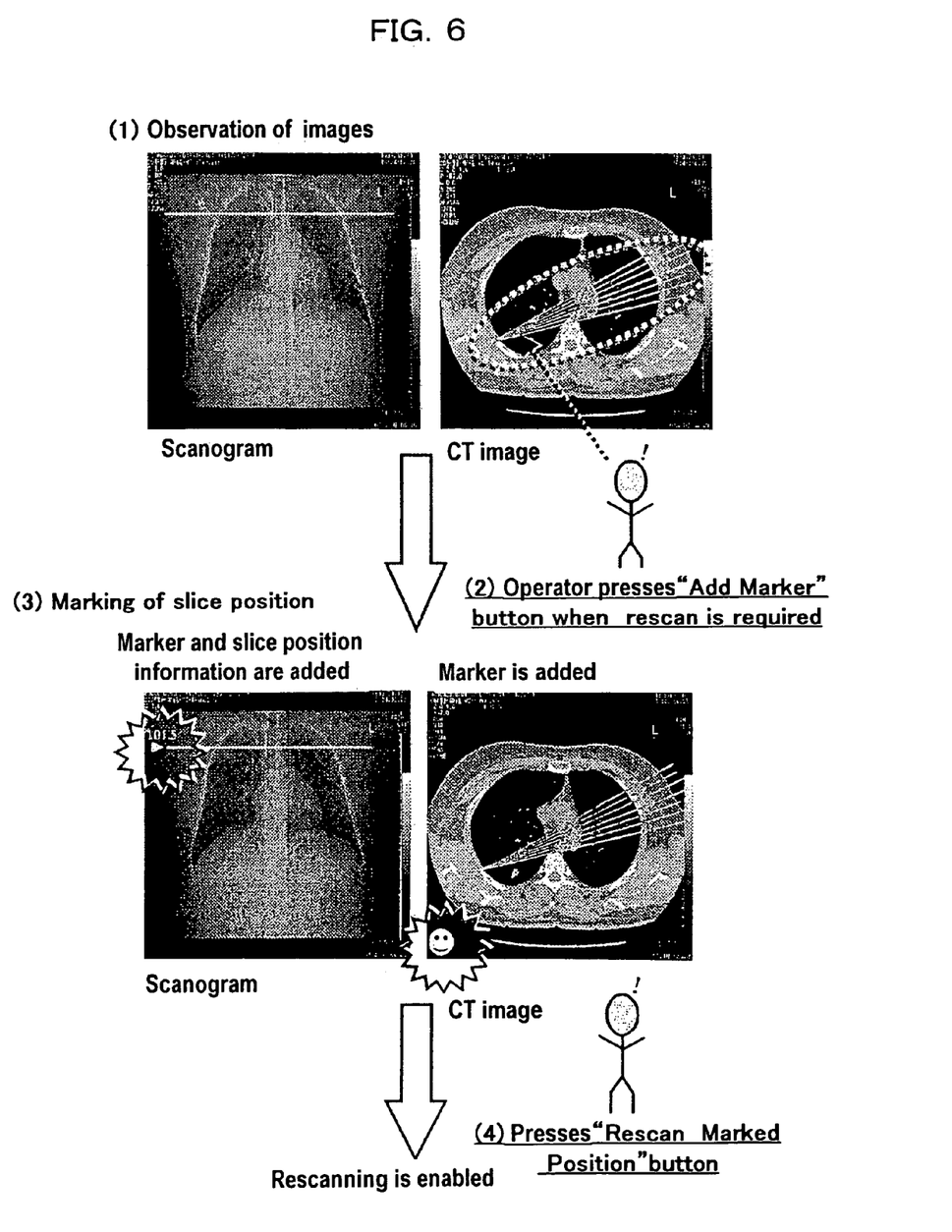
FIG. 6 is a view used to describe operations of adding a marker to a CT image to be re-scanned.

A CT image is interpreted (FIG. 6(1)), and the operator assesses whether the CT image is one in which an artifact has been generated due to movement by the subject (i.e., whether or not a rescan is necessary). If a rescan is necessary, the operator clicks on an "Add Marker" button using a mouse (FIG. 6(2)). When the "Add Marker" button is clicked, a marker is added to the CT image and a marker and slice position information is added to the scanogram (FIG. 6(3)).

<STEP S32>

CT imaging is performed for the purpose of rescanning. In this case, when a "Rescan Marked Position" button (for example, a software button displayed on the monitor) is clicked using the mouse, rescanning is performed for slice positions that have been added with a marker on the basis of the slice positions of the CT images for which the "Add Marker" button has been clicked.

Figure 7:
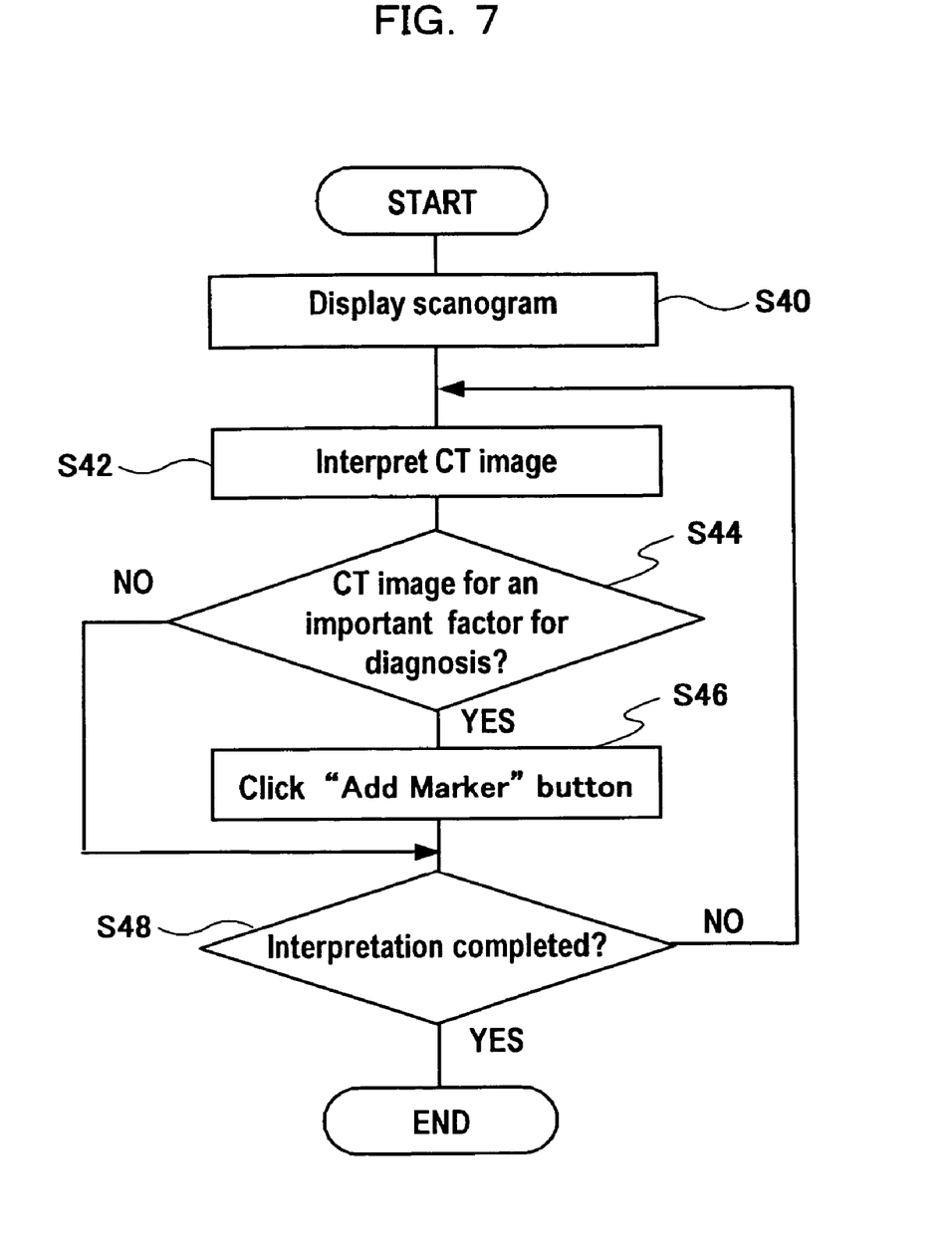
FIG. 7 is a flowchart illustrating a method of adding a marker to an image of diagnostic importance.

(3) Method for Adding Marker to Image as an Important Factor for Diagnosis in CRT Diagnosis FIG. 7 is a flowchart illustrating a method of adding a marker to an image that will be an important factor in diagnosis.

<STEP S40>

A CT image and scanogram stored in the storage device 20 of the operator console 18 are displayed on a monitor.

<STEP S42>

The displayed CT image is observed (interpreted).

<STEP S44>

Upon interpreting the CT image, judgment is made as to whether a CT image that will be an important factor in diagnosis is displayed.

<STEP S46>

When a CT image that will be an important factor in diagnosis is displayed, the operator clicks on the "Add Marker" button with the mouse. If the displayed CT image will not be an important factor in diagnosis the operation jumps to STEP S22.

When the "Add Marker" button is clicked, a marker is added to the CT image and a marker and slice position information are added to the scanogram.

<STEP S48>

Judgment is made as to whether all the CT images have been interpreted, and if all the images have not been interpreted the CT images are advanced by one frame and the above process from STEP S42 to STEP S46 is repeated.

By the above operations, markers are added to images that will be important factors in diagnosis, and markers and slice position information are added to the scanogram. The scanogram and CT images to which these markers and so forth have been attached are stored in the storage device 20.

Figure 8:
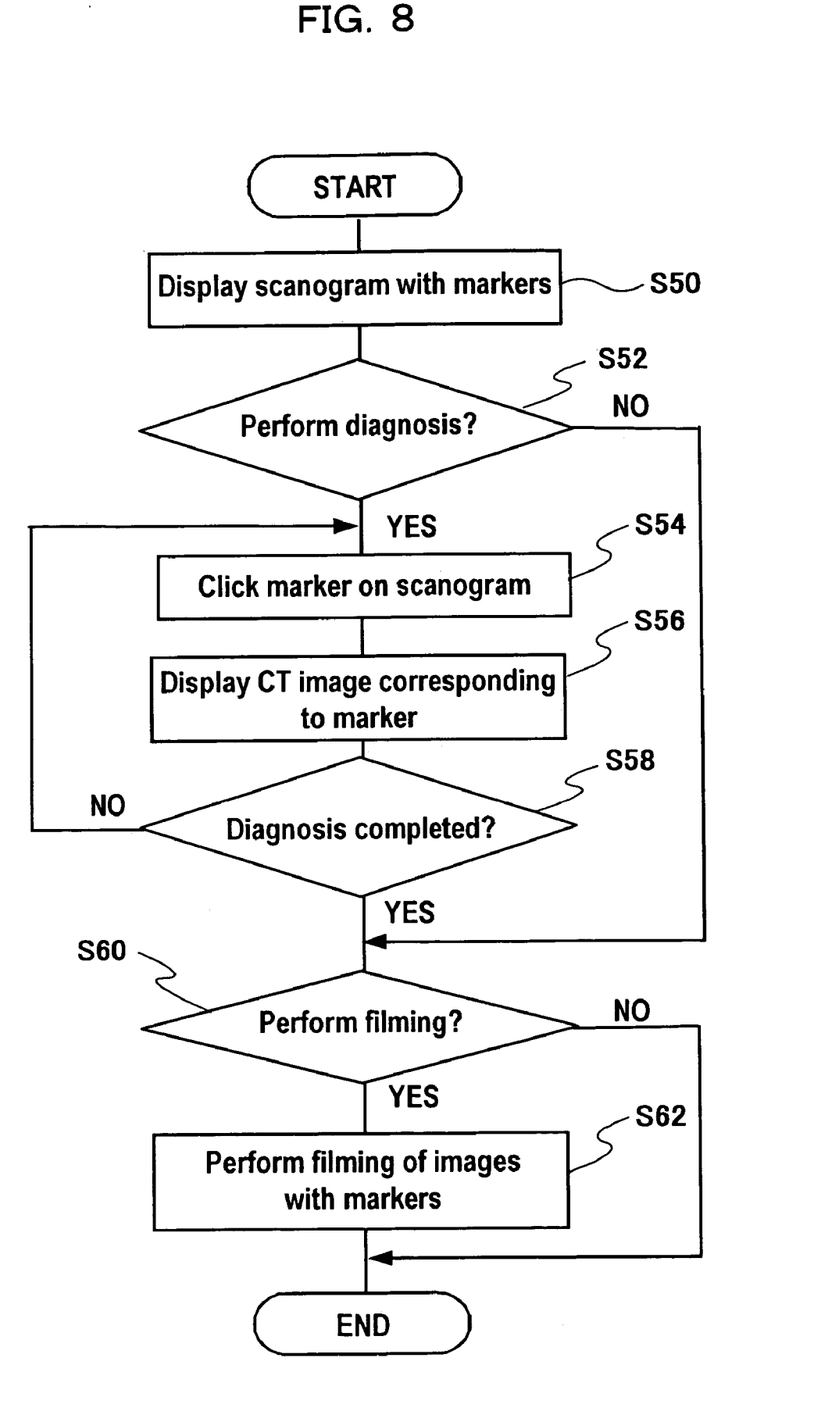
FIG. 8 is a flowchart illustrating a method of filming or re-displaying an image of diagnostic importance to which a marker was added.

(4) Method for Displaying Images Added with Markers as Important Factors in Diagnosis and Method for Filming the Images (Printing the Images on Film) in CT Examination FIG. 8 is a flowchart illustrating a method for filming or re-displaying an image to which a marker was added as an important factor in diagnosis in the above manner.

<STEP S50>

In order to perform diagnosis or filming, a scanogram added with a marker is readout from the storage 20 and displayed on a monitor.

<STEP S52>

If diagnosis is being performed the operation proceeds to STEP S54, and when diagnosis is not being performed the operation jumps to STEP S60.

<STEP S54>

Figure 9:
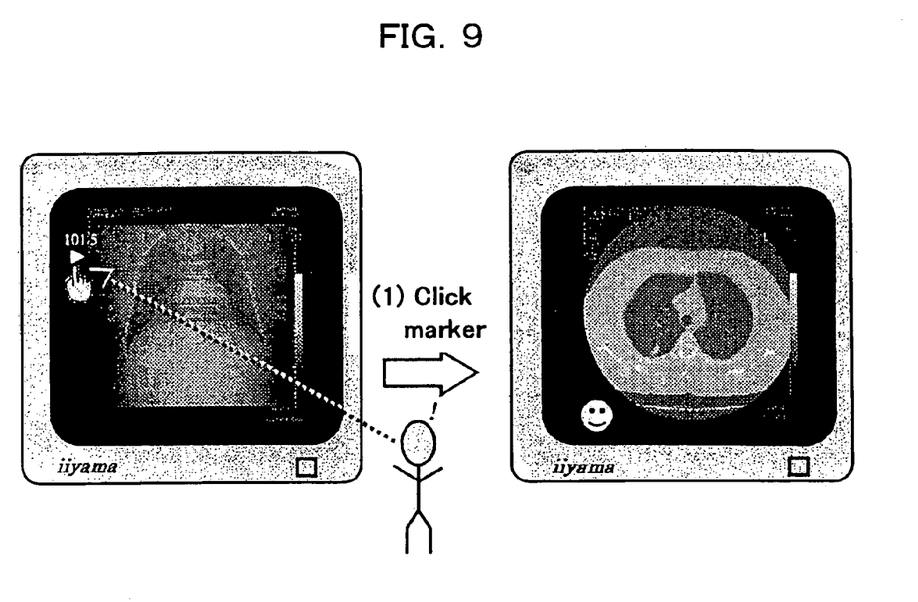
FIG. 9 is a view used to describe a method of displaying a CT image of diagnostic importance.

In order to deliver diagnosis, the marker on the scanogram is clicked using the mouse (FIG. 9(1)).

<STEP S56>

The CT image for the slice position that corresponds to the marker on the scanogram is readout from the storage device 20 and displayed on the monitor. Thus, a CT image that is an important factor in diagnosis can be displayed by just one click.

<STEP S58>

Judgment is made as to whether or not to terminate diagnosis. To display another CT image attached with a marker on the scanogram, the operation returns to STEP S54.

<STEP S60>

Judgment is made as to whether or not to perform filming of the scanogram and CT image(s).

<STEP S62>

Figure 10:
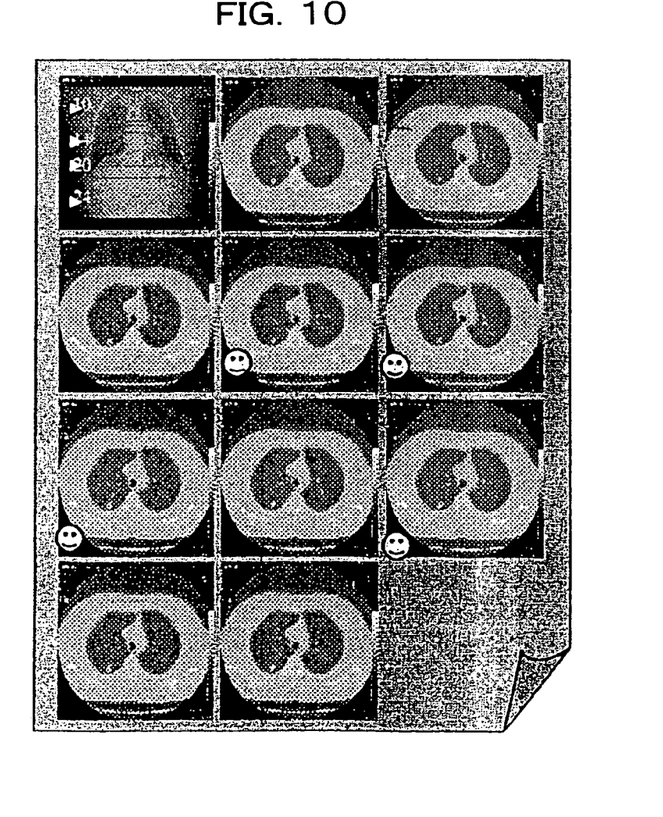
FIG. 10 is a view showing a film to which images including CT images of diagnostic importance printed.

When performing filming, if markers have been added to the scanogram and CT images, as shown in FIG. 10, the scanogram and CT images are subjected to filming in the state where the markers are added thereto.

When delivering diagnosis, the observer can interpret the CT images while paying particular attention to the images added with markers, and may insert a comment with respect to a CT image attached with a marker.

INDUSTRIAL APPLICABILITY

As described in the foregoing, according to the present invention the setting of a range for precise examination or slice positions for rescanning or the like can be performed accurately by a simple operation (for example, clicking a mouse) in a short time. It is thus possible to eliminate mistakes that occur when transcribing values for a range for precise examination or the like in a memo pad and mistakes that occur when setting the range or the like. Further, the time that a subject is bound to the CT apparatus can also be shortened. Since the slice positions can be handled as visual information in addition to numerical information, a range for precise examination or rescanning positions can be set with greater accuracy.

Further, since a tomogram that is an important factor for diagnosis can be displayed by simply designating a marker on a scanogram using a mouse or the like, for example, when diagnosis is delivered by a plurality of interpreters or the like, the second and subsequent interpreters can interpret the tomogram with better efficiency. Further, the method of adding a marker is extremely simple when compared with conventional input operations, such as text data, ROI, distance measurement, angle measurement, straight line, curved line, arrow and so forth, and since the method only involves adding a marker to the tomogram, there is no hindrance to observation of a lesion even in cases such as observing a state where a lesion is stained by a contrast medium over the course of time. The effect of the invention is manifested more noticeably as the number of images being handled increases, and it is particularly suited to observation of images that were taken using a multi-slice CT apparatus that generates a large quantity of images.

Furthermore, a tomogram that is an important factor for diagnosis can be simply found from among a plurality of tomograms on a film.

The invention claimed is:

1. A method for displaying images that displays a scanogram used for determining a scanning range of a subject to perform radiography of tomograms and also displays tomograms of a plurality of slice positions in a scanning range that is determined using the scanogram, comprising the steps of:
   sequentially displaying the plurality of tomograms to interpret the tomograms;
   designating a tomogram for precise examination or rescanning while interpreting the displayed tomograms; and
   adding a marker at a slice position on the scanogram corresponding to the designated tomogram.

2. The method for displaying images according to claim 1, wherein positional information that indicates the slice position is added together with the marker of the slice position added on the scanogram.

3. The method for displaying images according to claim 1, wherein positional information that indicates a slice position of the designated tomogram is stored in a storage device.

4. A method for performing radiography of image, comprising the steps of:
   performing radiography at a first slice thickness to obtain a plurality of tomograms from a predetermined scanning range of a subject;
   sequentially displaying the obtained plurality of tomograms to interpret the tomograms;
   designating tomograms to be subject to precise examination while interpreting the displayed tomograms;
   automatically setting a range for precise examination within the predetermined scanning range based on slice positions of the designated tomograms; and
   performing radiography of the automatically set range for precise examination at a second slice thickness that is thinner than the first slice thickness.

5. The method for performing radiography of image according to claim 4, further comprising a step of performing radiography of a scanogram of the subject to determine the predetermined scanning range.

6. The method for performing radiography of image according to claim 4, wherein the step of designating tomograms to be subject to precise examination designates two tomograms as a first and last tomogram of precise examination, and the step of automatically setting a range for precise examination sets a region between the slice positions of the two tomograms as a range for precise examination.

7. The method for performing radiography of image according to claim 4, wherein the step of designating tomograms to be subject to precise examination designates one tomogram to be subject to precise examination, and the step of automatically setting a range for precise examination sets a predetermined range that includes the one tomogram and tomograms prior to and after the one tomogram as a range for precise examination.

8. The method for imaging according to claim 4, wherein the step of designating tomograms to be subject to precise examination designates a plurality of tomograms to be subject to precise examination, and the step of automatically setting a range for precise examination sets a range that covers the plurality of tomograms as a range for precise examination.

9. A method for displaying images that displays a scanogram used for determining a slice range or slice positions of a subject to perform radiography of tomograms, and also displays tomograms of a plurality of slice positions taken within a slice range determined using the scanogram, comprising the steps of:
   sequentially displaying the plurality of tomograms to interpret the tomograms;
   designating a tomogram as an important factor for diagnosis while interpreting the displayed tomograms; and
   adding a first marker at a slice position on the scanogram corresponding to the designated tomogram.

10. The method for displaying images according to claim 9, further comprising a step of displaying the designated tomogram of the slice position indicated by the first marker when an optional first marker is designated on the scanogram to which the first marker was added.

11. The method for displaying images according to claim 9, wherein a second marker is added on the designated tomogram to indicate including an important factor for diagnosis.

12. The method for displaying images according to claim 11, further comprising a step of printing on a film a scanogram on which the first marker was added and a view of tomograms that contains tomograms to which the second marker was added.

* * * * *